(12) United States Patent
Bombeck et al.

(10) Patent No.: US 12,257,441 B2
(45) Date of Patent: Mar. 25, 2025

(54) MINIMALLY INVASIVE NEUROSTIMULATION DEVICE

(71) Applicant: Medtronic, Inc., Minneapolis, MN (US)

(72) Inventors: Charles Bombeck, Lino Lakes, MN (US); Sarah Offutt, Golden Valley, MN (US); Ryan Bauer, Plymouth, MN (US); Andrew Cleland, St. Paul, MN (US); Randy S. Roles, Elk River, MN (US)

(73) Assignee: Medtronic, Inc., Minneapolis, MN (US)

( * ) Notice: Subject to any disclaimer, the term of this patent is extended or adjusted under 35 U.S.C. 154(b) by 69 days.

(21) Appl. No.: 18/307,385

(22) Filed: Apr. 26, 2023

(65) Prior Publication Data

US 2023/0256254 A1    Aug. 17, 2023

Related U.S. Application Data

(62) Division of application No. 16/947,092, filed on Jul. 17, 2020, now Pat. No. 11,672,991.

(60) Provisional application No. 62/875,089, filed on Jul. 17, 2019.

(51) Int. Cl.
*A61N 1/372* (2006.01)
*A61B 34/00* (2016.01)
*A61N 1/05* (2006.01)
*A61N 1/378* (2006.01)

(52) U.S. Cl.
CPC ....... *A61N 1/37235* (2013.01); *A61N 1/0504* (2013.01); *A61N 1/0558* (2013.01); *A61N 1/378* (2013.01); *A61B 2034/252* (2016.02)

(58) Field of Classification Search
None
See application file for complete search history.

(56) References Cited

U.S. PATENT DOCUMENTS

| | | | |
|---|---|---|---|
| 9,076,187 B1 | 7/2015 | Laing et al. |
| 9,398,901 B2 | 7/2016 | Tischendorf et al. |
| 9,585,642 B2 | 3/2017 | Dinsmoor et al. |
| 9,826,963 B2 | 11/2017 | Scott et al. |
| 9,931,107 B2 | 4/2018 | Tischendorf et al. |
| 10,258,789 B2 | 4/2019 | Tischendorf et al. |
| 10,299,987 B2 | 5/2019 | Greiner et al. |
| 10,583,284 B2 | 3/2020 | Peters et al. |
| 11,672,991 B2 | 6/2023 | Bombeck et al. |

(Continued)

OTHER PUBLICATIONS

Peters et al., The Future of Neuromodulation, Adult and Pediatric Neuromodulation, pp. 185-197, Mar. 21, 2018.

(Continued)

*Primary Examiner* — Michael W Kahelin
(74) *Attorney, Agent, or Firm* — Husch Blackwell LLP

(57) ABSTRACT

Aspects of the present disclosure are directed to an implantable medical device including a housing containing components therein configured for delivering neurostimulation therapy, and an anchoring feature included with the housing. The implantable medical device also includes a lead having an electrode. In one aspect, the implantable medical device may include a guidewire passageway configured to allow the lead of implantable medical device to be introduced over a guidewire.

6 Claims, 13 Drawing Sheets

(56) References Cited

U.S. PATENT DOCUMENTS

| | | | |
|---|---|---|---|
| 2014/0163580 A1* | 6/2014 | Tischendorf | A61N 1/3756 607/116 |
| 2014/0288613 A1 | 9/2014 | Laing et al. | |
| 2017/0095667 A1 | 4/2017 | Yakovlev et al. | |
| 2017/0333702 A1 | 11/2017 | Barner | |
| 2018/0161576 A1 | 6/2018 | Ostroff et al. | |
| 2018/0256906 A1 | 9/2018 | Pivonka et al. | |
| 2019/0070420 A1 | 3/2019 | Oron et al. | |

OTHER PUBLICATIONS

MacDiarmid et al., Feasibility of a Fully Implanted, Nickel Sized and Shaped Tibial Nerve Stimulator for the Treatment of Overactive Bladder Syndrome with Urgency Urinary Incontinence, The Journal of Urology, vol. 21, pp. 967-972, May 2019.

Heesakkers et al., A novel leadless, miniature implantable Tibial Nerve Neuromodulation System for the management of overactive bladder complaints, Neurourology and Urodynamics, pp. 1-8, Sep. 11, 2017.

Van Breda et al., A new implanted posterior tibial nerve stimulator for the treatment of overactive bladder syndrome, three-months results of a novel therapy in a single center, Journal of Urology, Chapter 5.2, Feb. 9, 2019.

Sievert, Implantable Chronic Tibial Nerve Modulation (CTNM), Neurourology, pp. 321-325, Mar. 12, 2019.

Van Der Pal et al., Percutaneous tibial nerve stimulation in the treatment of refractory overactive bladder syndrome: is maintenance treatment necessary?, BJU International, vol. 97, Issue 3, pp. 547-550, Sep. 30, 2005.

Application and file history for U.S. Appl. No. 16/947,092, filed Jul. 17, 2020, issued as U.S. Pat. No. 11,672,991 on Jun. 13, 2023, inventors Bombeck et al.

* cited by examiner

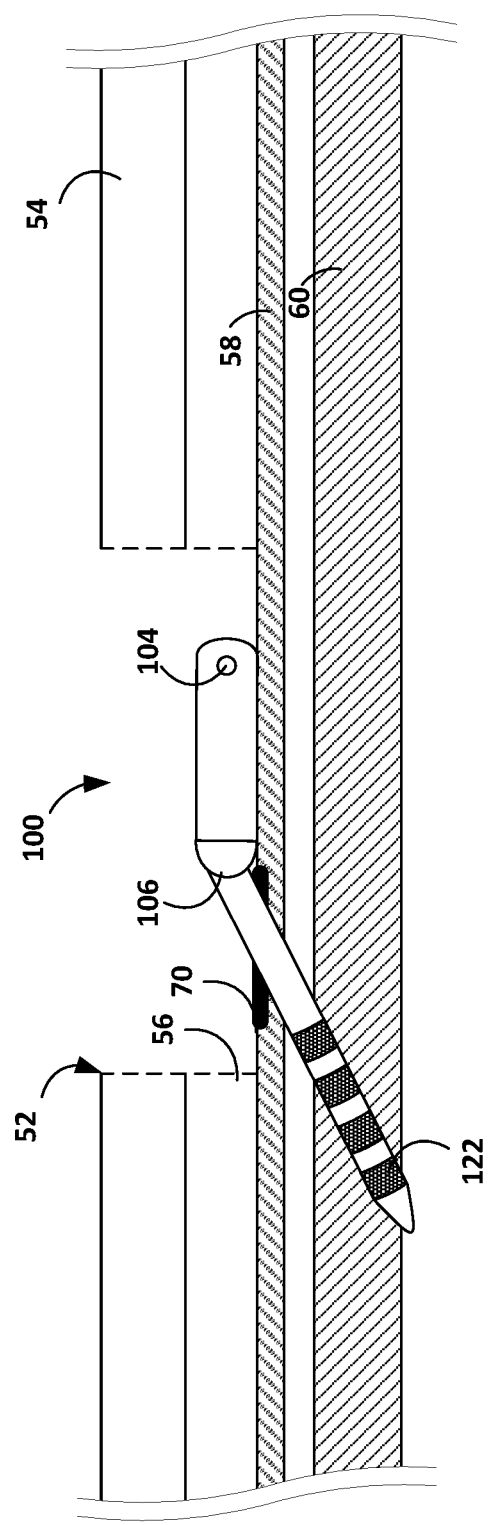

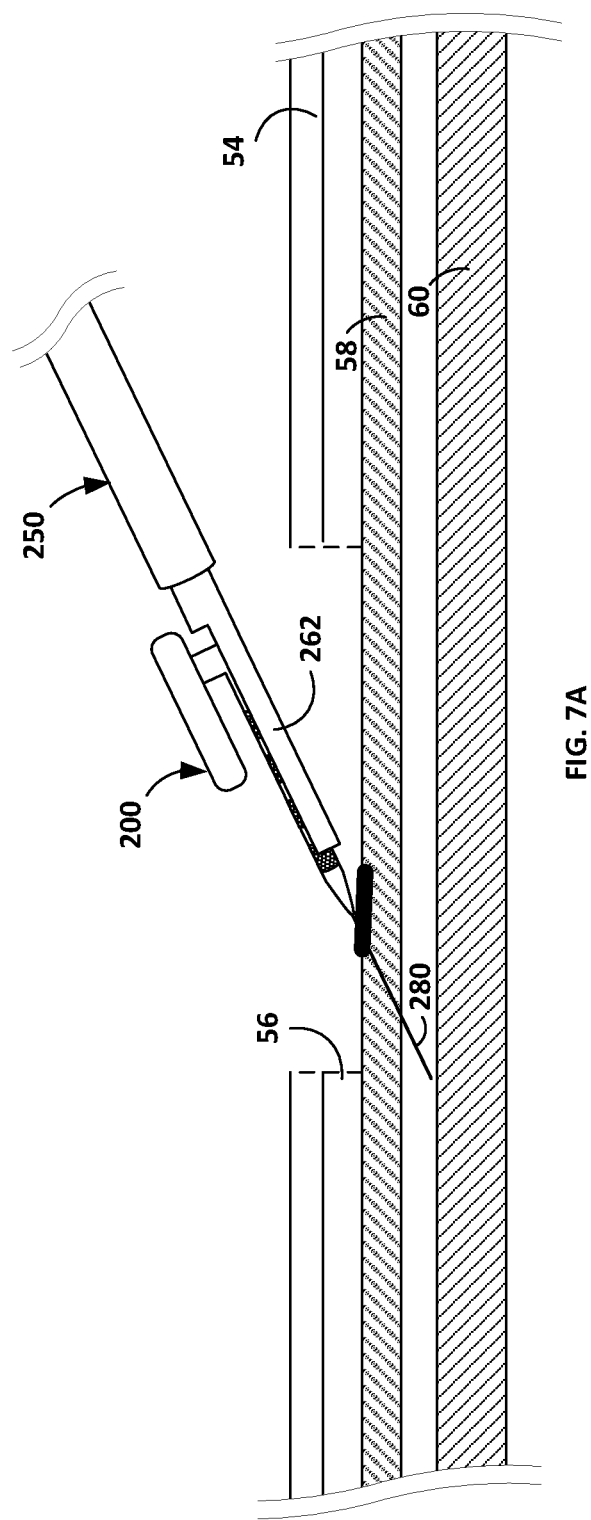

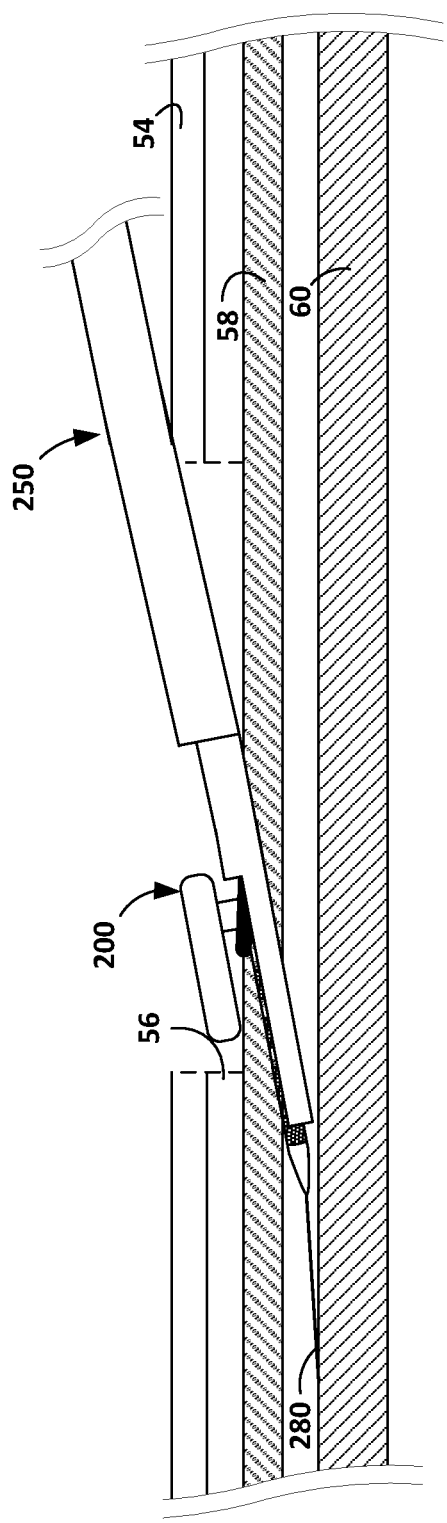

MINIMALLY INVASIVE NEUROSTIMULATION DEVICE

CROSS-REFERENCE TO RELATED APPLICATIONS

The present application is a divisional of U.S. application Ser. No. 16/947,092 filed Jul. 17, 2020, which claims the benefit of U.S. Provisional Application No. 62/875,089 filed Jul. 17, 2020, the disclosures of which are hereby incorporated by reference in their entireties.

FIELD

The disclosure relates generally to implantable neurostimulation systems, and in particular to minimally invasive implantable neurostimulation systems.

BACKGROUND

Implantable medical devices may be configured to deliver electrical stimulation therapy and/or monitor physiological signals. Electrical stimulation of nerve tissue, for example, may provide relief for a variety of disorders, improving the quality of life for many patients.

Some implantable medical devices (IMDs) may employ electrical leads that carry electrodes. For example, electrodes may be located at a distal portion of an elongate lead. Other examples of electrical leads may be relatively short, having one or more electrodes located along a body of the lead. Electrical leads may be releasably coupled to, or integrated with, a housing of the IMD.

SUMMARY

In one aspect, the present disclosure is directed to an implantable medical device including a housing containing components therein configured for delivering neurostimulation therapy, and an anchoring feature included with the housing. The implantable medical device also includes a lead having an electrode. In one aspect, implantable medical device may include a guidewire passageway configured to allow the lead of implantable medical device to be introduced over a guidewire.

In another aspect, the disclosure is directed to a system including an implantable medical device having a housing with components disposed therein configured for delivering neurostimulation therapy. The housing further includes an anchoring feature. The implantable medical device also includes a lead having an electrode. The system further includes an implant tool configured to be used during implantation of the medical device.

In another aspect, the disclosure is directed to an implantable tibial nerve stimulation device, comprising a housing including electronic circuitry disposed within the housing and configured for delivering tibial nerve stimulation therapy, communication circuitry and related components disposed within the housing, the communication circuitry and related components configured for at least one of receiving programming instructions from an external programmer or providing feedback to an external device, and a power source disposed within the housing, wherein the housing includes a longitudinal axis. The implantable nerve stimulation device further comprises an electrical lead including at least one electrode, the electrical lead including a longitudinal axis, wherein the electrical lead is offset from the housing and further wherein the electrical lead longitudinal axis is generally oriented in the same direction as the housing longitudinal axis, and wherein the electrical lead is connected to the electronic circuitry disposed within the housing such that the tibial nerve stimulation therapy is deliverable via the at least one electrode.

In another aspect, the disclosure is directed to a system, comprising an implantable tibial nerve stimulation device including a housing comprising electronic circuitry disposed within the housing and configured for delivering tibial nerve stimulation therapy, communication circuitry and related components disposed within the housing, the communication circuitry and related components configured for at least one of receiving programming instructions from an external programmer or providing feedback to an external device, and a power source disposed within the housing, wherein the housing includes a longitudinal axis. The implantable nerve stimulation device further comprises an electrical lead including at least one electrode, the electrical lead including a longitudinal axis, wherein the electrical lead is offset from the housing and further wherein the electrical lead longitudinal axis is generally oriented in the same direction as the housing longitudinal axis, wherein the electrical lead is connected to the electronic circuitry disposed within the housing such that the tibial nerve stimulation therapy is deliverable via the at least one electrode. The system further comprises an implant tool including an outer sheath and an inner sheath, the inner sheath including a cradle portion configured to selectively carry the implantable tibial nerve stimulation device.

In another aspect, the disclosure is directed to a method, comprising providing an implantable tibial nerve stimulation device to a user, the implantable tibial nerve stimulation device including a housing comprising electronic circuitry disposed within the housing and configured for delivering tibial nerve stimulation therapy, communication circuitry and related components disposed within the housing, the communication circuitry and related components configured for at least one of receiving programming instructions from an external programmer or providing feedback to an external device, and a power source disposed within the housing, wherein the housing includes a longitudinal axis, and an electrical lead including at least one electrode, the electrical lead including a longitudinal axis, wherein the electrical lead is offset from the housing and further wherein the electrical lead longitudinal axis is generally oriented in the same direction as the housing longitudinal axis, wherein the electrical lead is connected to the electronic circuitry disposed within the housing such that the tibial nerve stimulation therapy is deliverable via the at least one electrode. The method further comprises providing instructions recorded on a tangible medium to the user, the instructions for implanting the tibial nerve stimulation device in an ankle region of a patient, the instructions comprising creating a first incision, in a skin of a patient superior and posterior to a medial malleolus on an ankle of the patient, creating a second incision, in a fascia layer in the ankle of the patient, the second incision being smaller than the first incision and the second incision sized to allow passage of the electrical lead therethrough, and advancing the implantable tibial nerve stimulation device through the first incision downward towards a heel of the patient and inward such that the electrical lead passes through the second incision, such that the housing of the implantable tibial nerve stimulation device is positioned superficial to the fascia layer and such that the at least one electrode is positioned below the fascia.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIGS. 3A-3C are schematic representations of an implant procedure for a medical device according to an embodiment of the disclosure.

FIGS. 7A-7C are schematic representations of an implant procedure for a medical device according to another embodiment of the disclosure.

DETAILED DESCRIPTION

Embodiments of implantable medical devices described herein may be useful for numerous types of neurostimulation therapies, such as for pain control, autonomic nervous system modulation, functional electrical stimulation, tremor, and more. Embodiments of implantable medical devices described herein may be useful for stimulating one or more nerves to control symptoms of overactive bladder, urgency frequency, nocturia, painful bladder syndrome, chronic pelvic pain, incontinence, or other pelvic health conditions. These embodiments may also be useful for stimulating one or more peripheral nerves to control pain in one or more areas of the body, such as a foot, ankle, leg, groin, shoulder, arm, wrist, or the back, for example. In one example, embodiments of implantable medical devices described herein may be used to stimulate a tibial nerve of a patient.

Figure 1:
FIGS. 1 and 2 are schematic representations of an ankle area of a patient.
Figure 2:
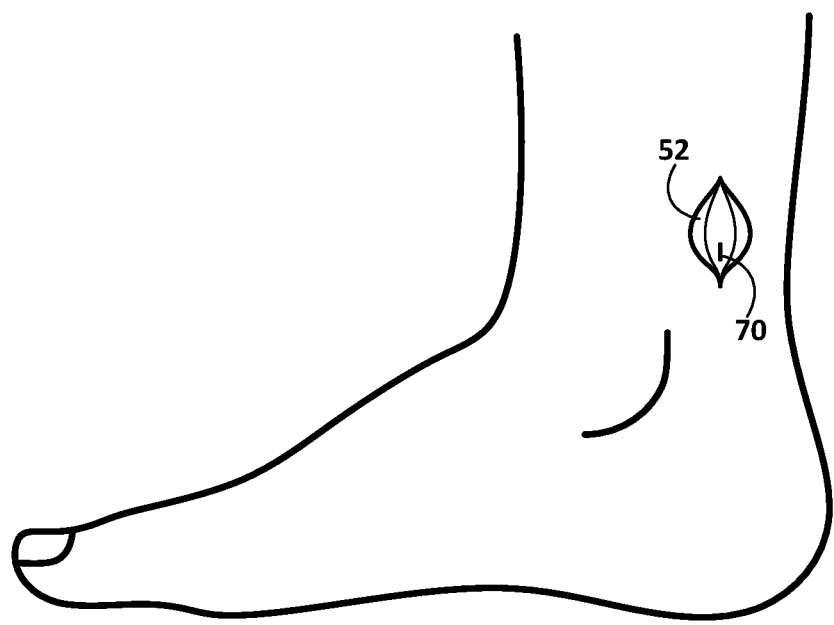
Figure 3A:
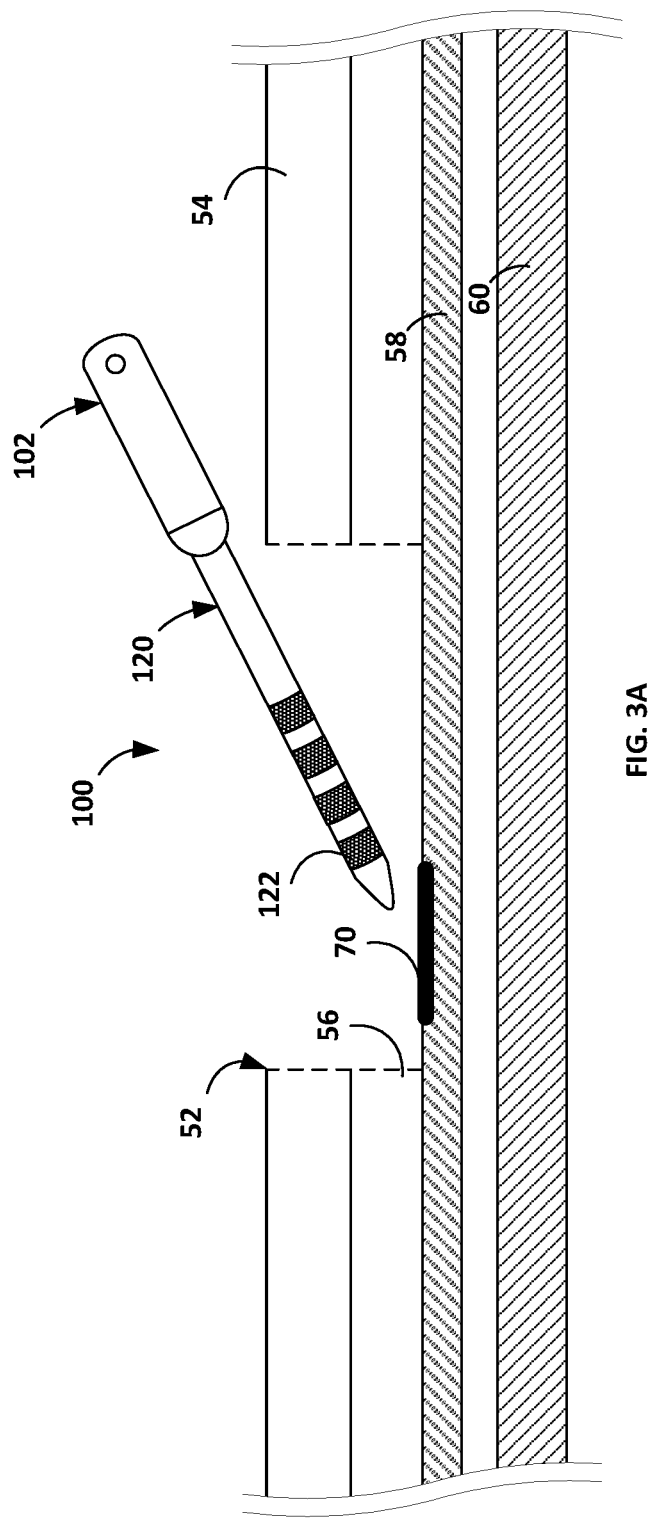
Figure 3B:
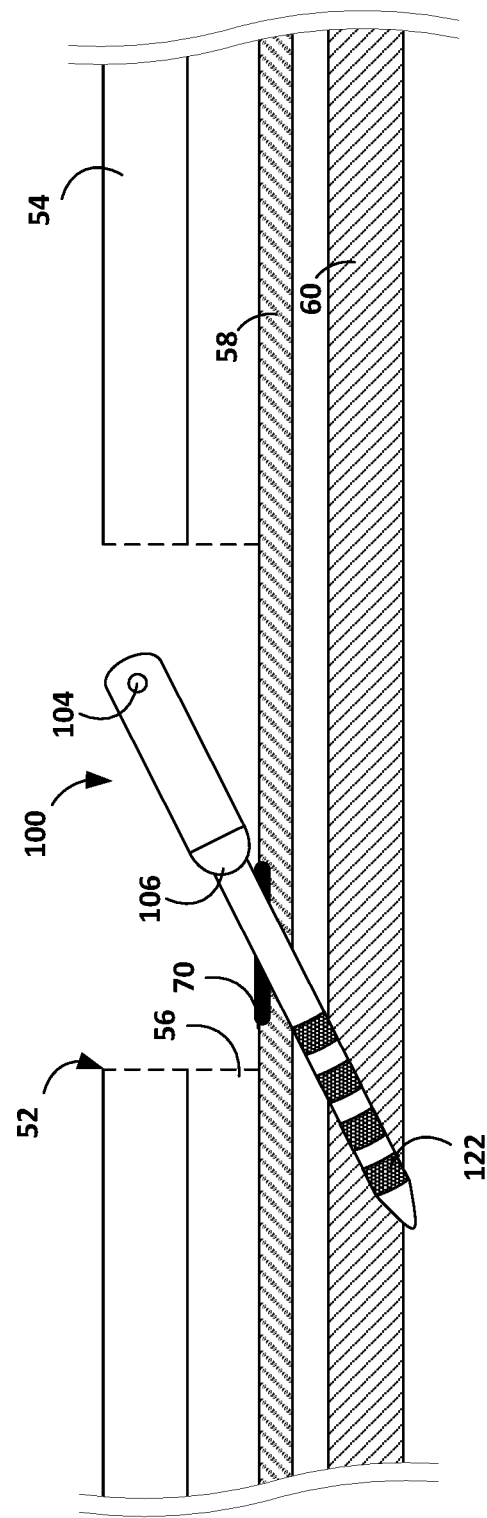

Referring now to FIGS. 3A-3C, an IMD 100 is depicted. IMD 100 generally includes a housing 102, and a lead 120. Housing 102 includes electronic circuitry and associated components therein, e.g., comprising one or more electronic circuits for delivering electrical stimulation therapy. Housing 102 can also include communication circuitry disposed therein for receiving programming communication from an external programmer, or providing feedback to a programmer or other external device.

In one example, housing 102 can include an energy source enclosed therein, e.g., a battery. In another example, IMD 100 can be configured to receive energy signals from an external device and transduce the received energy signals into electrical power that is used to recharge a battery of IMD 100. In one example, IMD 100 may be configured to receive energy signals from an external device and transduce the received energy signals into electrical power that is used to power the device to deliver electrical stimulation therapy.

IMD 100 can include one or more fixation elements or anchor features 104 such as suture tabs or apertures, tines, barbs, or other suitable passive or active fixation elements. As depicted in FIGS. 3A-3C, housing 102 of IMD 100 includes an aperture 104 configured to facilitate securing housing 102 to a patient by the use of a suture, clip, or other surgical fastening tools. Housing 102 can also include a shoulder or flange portion 106.

Lead 120 can include one or more electrodes 122 arranged thereon. As depicted in FIGS. 3A-3C, electrodes 122 are approximately equally spaced along a length of lead 120. However, alternate arrangements are within the scope of the invention, such as a greater or lesser number of electrodes, unequal spacing of electrodes, and different types of electrodes. Suitable electrode types can include ring electrodes, tip electrodes, coil electrodes, and others. Lead 120 can be referred to as a stubby lead, or pigtail lead.

Lead 120 can be flexible, semi-rigid, or rigid. In an example, lead 120 can be removably coupled to housing 102. In other examples, lead 120 can be non-removably coupled to or integrally formed with housing 102. The connection between lead 120 and housing 102 can include a flexible joint or hinge. Although not depicted in the Figures, lead 120 can include one or more fixation elements or features such as tines, barbs, suture tabs, or other suitable passive or active fixation elements as known in the art.

Referring now to FIGS. 1-3C, a method of implanting IMD 100 proximate a tibial nerve will be described. On an ankle 50 of a patient, a first incision 52 in skin 54 is made. First incision 52 can be a one to five cm axial incision superior and posterior to a medial malleolus and above a tibial nerve 60 on a medial aspect of ankle 50. In another example, first incision 52 can be in a range of one to three cm long. With first incision 52 made, a medical practitioner can dissect down through fat layers 56 to fascia 58. With fascia 58 exposed, a second incision or nick 70 is made in fascia 58 at an inferior end (toward a heel of the patient) of the dissected area. In an example, second incision 70 is smaller than first incision 52.

In an example, the size of second incision 70 is chosen to allow lead 120 of IMD 100 to pass therethrough but not allow housing 102 to pass therethrough. In an example, second incision 70 and lead 120 can be appropriately sized to provide a friction fit therewith. In an example, second incision 70 can be sized such that passage of lead 120 through second incision 70 causes stretching of second incision 70 to accommodate lead 120. In an example, IMD 100 may include a shoulder portion 106 sized and shaped to prevent passage of housing 102 through second incision 70. In another example, housing 102 may itself be sized and shaped larger than lead 120 to prevent passage of housing 102 through second incision 70.

Lead 120 may then be inserted through second incision 70 inward toward tibial nerve 60 and inferiorly toward the heel, as depicted in FIG. 3B. Prior to anchoring housing 102, optional testing of IMD 100 may be performed to determine if lead 120 has been properly positioned close to tibial nerve 60 to elicit a desired response from an applied electrical stimulation. In an example, IMD 100 is controlled by an external programmer to deliver test stimulation, and one or more indicative responses are monitored, such as toe flexion from simulation of the tibial motor neurons controlling the flexor hallucis brevis or flexor digitorum brevis, or a tingling sensation in the heel or sole of the foot excluding the medial arch. If such testing does not elicit appropriate motor or sensory responses, the practitioner should withdraw and reposition lead 120 and retest.

In an example, proper positioning of lead 120 is achieved with electrodes 122 inward of fascia 58 and in close proximity to tibial nerve 60, wherein tibial nerve 60 is commonly located about one to six millimeters deep to fascia 58 in the region of ankle 50 which is superior to the medial malleolus.

Once a practitioner has determined lead 120 is properly positioned to provide an appropriate patient response to delivered stimulation therapy, housing 102 can be secured in place such as in FIG. 3C. In an example, a suture or similar surgical fastening means can be attached between anchor feature 104 of housing 102 and surrounding tissue of the patient. Thus IMD 100 is therefore fixed in position at two points, with housing 102 secured by way of anchor feature 104 and lead 120 secured at second incision 70. In another example, housing 102 is not anchored with any surgical fastening means, and retention of housing 102 can be accomplished by an interference fit against tissue in and around the implant site. First incision 52 can then be closed by appropriate means.

Figure 4B:
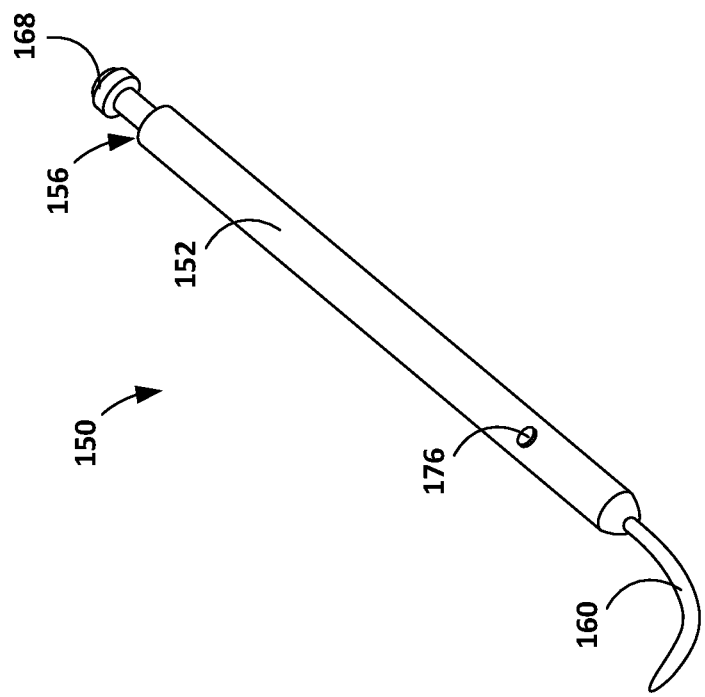
FIG. 4B is a perspective view of an implant tool according to another embodiment of the disclosure.
Figure 4A:
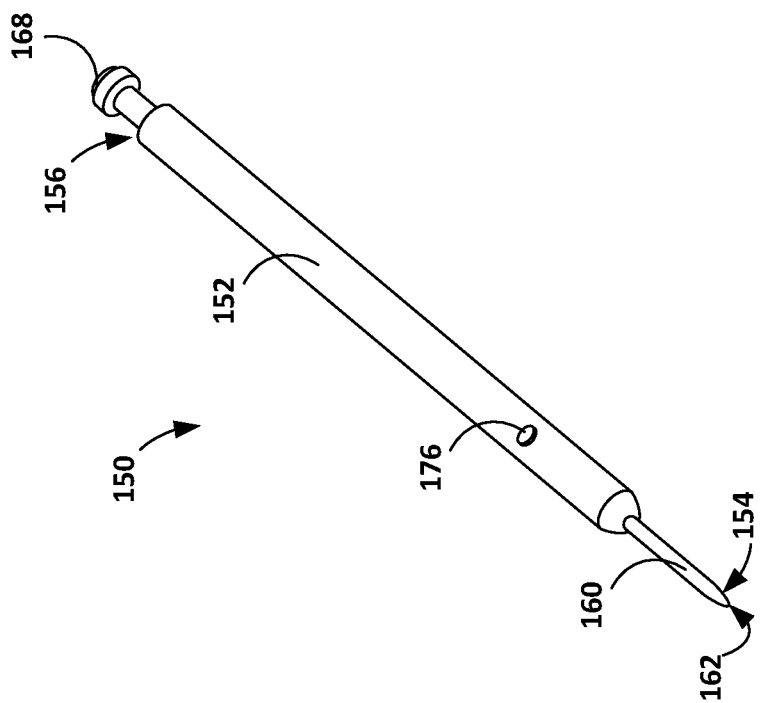
FIG. 4A is a perspective view of an implant tool according to an embodiment of the disclosure.
Figure 4C:
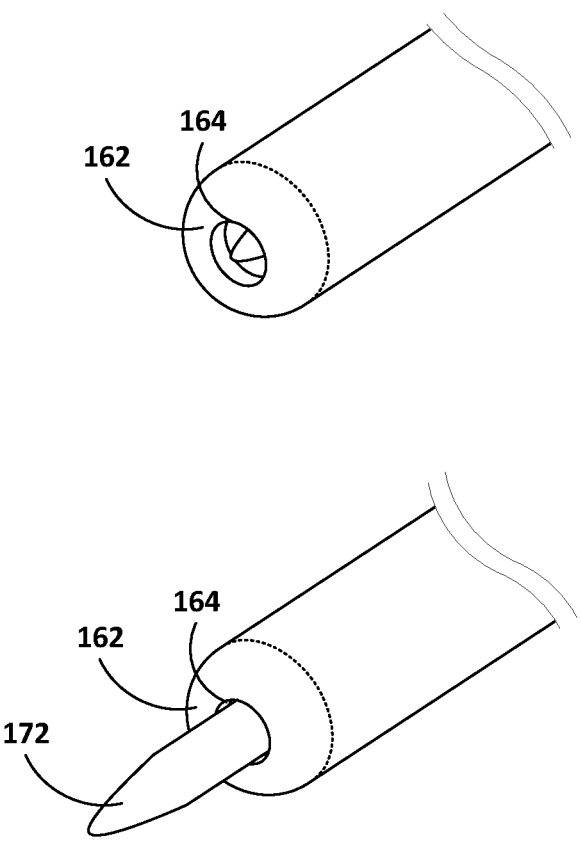
FIG. 4C is a close up view of an implant tool in a retracted position and in a deployed position, according to an embodiment of the disclosure.

Referring now to FIGS. 4A-4C, a tool 150 can be utilized during the implant procedure. Tool 150 includes a body or handle 152 suitable for being grasped by a practitioner, and a first end 154 and a second end 156. First end 154 can include a shaft portion 160 which terminates in a rounded or blunt tip 162, and a port 164 defined in tip 162. In an example, shaft portion 160 can have a diameter less than a diameter of body 152. In another example, shaft portion 160 can have a diameter approximately similar to a diameter of lead 120. In an example depicted in FIG. 4A shaft portion 160 can be generally straight and aligned with handle 152. In another example depicted in FIG. 4B, shaft portion 160 can have a curved profile.

Second end 156 of tool 150 can include an actuator 168. In another example, actuator 168 can be located along body 152. Actuator 168 is operably coupled to a movable piercing element 172 disposed within tool 150. Referring to FIG. 4C, piercing element 172 is movable by way of actuator 168 between a retracted position (top) wherein piercing element 172 is contained within tool 150, and a deployed position (bottom) wherein a tip of piercing element 172 protrudes from port 164. Piercing element 172 can be sized and shaped to easily create a second incision 70 appropriately sized for passage of lead 120 therethrough. In another example, piercing element 172 may be a conventional guidewire, manually manipulated through a passageway within tool 150 and exiting through port 164.

In an example, tool 150 is configured such that the default position of piercing element 172 is in the retracted position, and moving piercing element 172 to the deployed position locks piercing element 172 in the deployed position. A release mechanism 176 can be included in tool 150 to release piercing element 172 from the deployed position and return piercing element 172 to the retracted position.

In operation, tool 150 can be used by a practitioner to dissect tissue at the implant site and create a predictably sized second incision 70 in fascia 58. After first incision 52 is created, and the fascia is exposed, a practitioner can operate the actuator 168 of the tool 150 to move piercing element 172 from the retracted position to the deployed position. A practitioner can then utilize tool 150 with piercing element 172 in the deployed position to create second incision 70 at a desired location in fascia 58. A practitioner can then operate actuator 176 to move the piercing element 172 from a deployed to a retracted position as the shaft of the tool 160 is advanced through the second incision 70. With the piercing element 172 retracted the shaft of the tool 160 can be used to bluntly dissect a path for the lead 120 through the tissues below the fascia with minimal risk of piercing or rupturing a blood vessel or tendon sheath. Positioning and securing lead 120 and housing 102 can then be accomplished as described above.

Figure 5A:
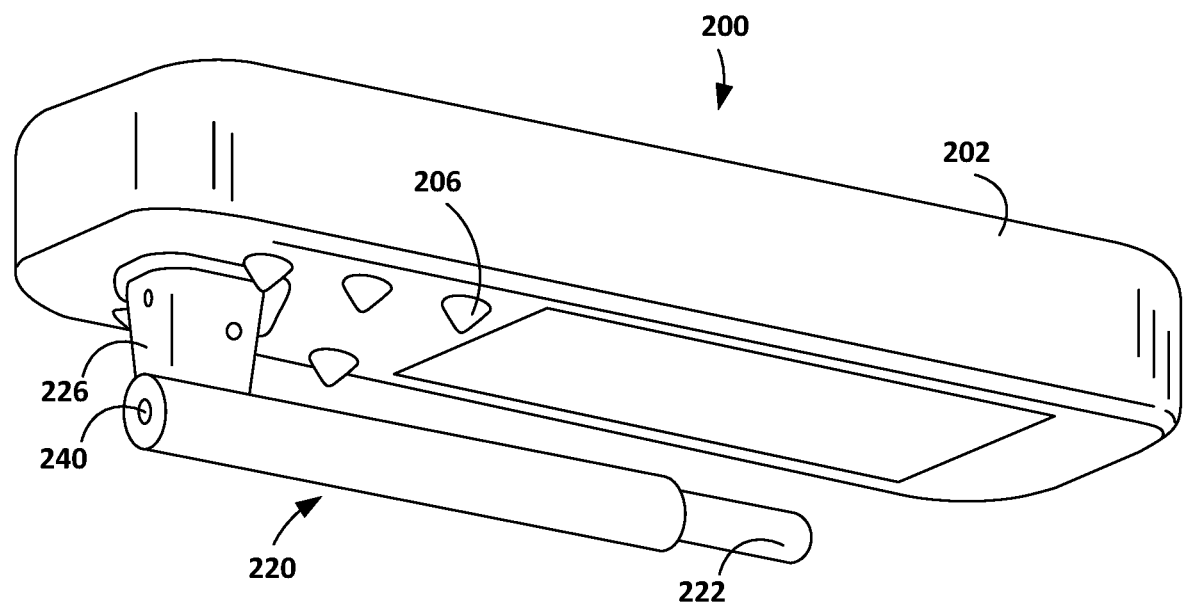
FIG. 5A is a perspective view of an implantable medical device according to an embodiment of the disclosure.
Figure 5B:
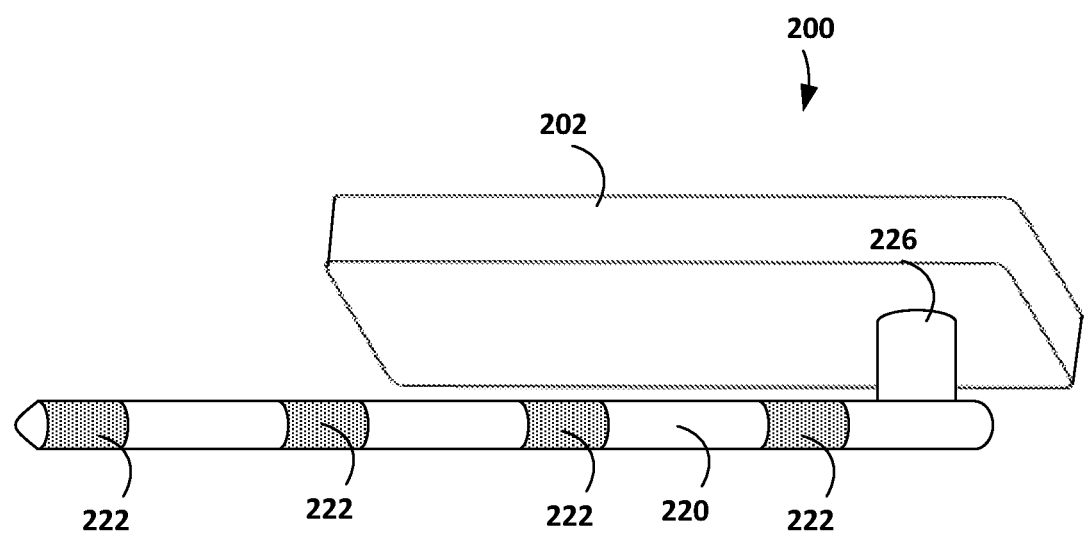
FIG. 5B is a perspective view of an implantable medical device according to another embodiment of the disclosure.

Referring now to FIGS. 5A and 5B, an IMD 200 is depicted as another example of the present disclosure. IMD 200 is configured for implantation using a guidewire, and IMD 200 generally includes a housing 202, a lead 220, and a guidewire passageway 240. The embodiments of IMD 200 have many similarities to the embodiments of IMD 100 described above and for simplicity the description of all common components is not repeated in the following, and like numerals may designate like parts throughout that are corresponding or analogous.

IMD 200 can include one or more fixation elements or anchor features such as suture tabs or apertures, tines, barbs, or other suitable passive or active fixation elements. As depicted in FIG. 5A, housing 202 includes a plurality of passive fixation elements in the form of protrusions 206 disposed on housing 202. Although not depicted in the Figures, IMD 200 can include additional fixation or anchoring elements, such as a tab or loop configured to facilitate securing housing 202 to a patient by the use of a suture, clip, or other surgical fastening tools.

Lead 220 can include one or more electrodes 222 arranged thereon. As depicted in FIG. 5A, lead 220 includes one electrode 222 disposed near a tip of lead 220. In the embodiment of FIG. 5B, lead 220 includes a plurality of electrodes 222 which are approximately equally spaced along a length of lead 220. However, alternate arrangements are within the scope of the invention, such as a greater or lesser number of electrodes, unequal spacing of electrodes, and different types of electrodes. Suitable electrode types can include ring electrodes, tip electrodes, coil electrodes, and others. Lead 220 can be referred to as a stubby lead, or pigtail lead.

As depicted in FIGS. 5A-5B, IMD 200 includes a structure 226 for coupling lead 220 to housing 202. Structure 226 can be configured to create a desired alignment or orientation of lead 220 with respect to housing 202. Further, a longitudinal axis of lead 220 is oriented generally parallel with a longitudinal axis of housing 202, although other configurations are possible. Structure 226 can be flexible, semi-rigid, or rigid. Similarly, lead 220 can be flexible, semi-rigid, or rigid. In an example, lead 220 can be removably coupled to housing 202. In other examples, lead 220 can be non-removably coupled to or integrally formed with housing 202. The connection between lead 220 and housing 202 can include a flexible joint or hinge. Although not depicted in the Figures, lead 220 can include one or more fixation elements or features such as tines, barbs, suture tabs, or other suitable passive or active fixation elements as known in the art.

IMD 200 is configured for implantation over a guidewire, and IMD 200 includes a guidewire passageway 240 which can be included as part of, or coupled with, housing 202, lead 220, structure 226, or a combination thereof. As depicted in FIG. 5A for example, guidewire passageway 240 extends through lead 220.

Figure 6A:
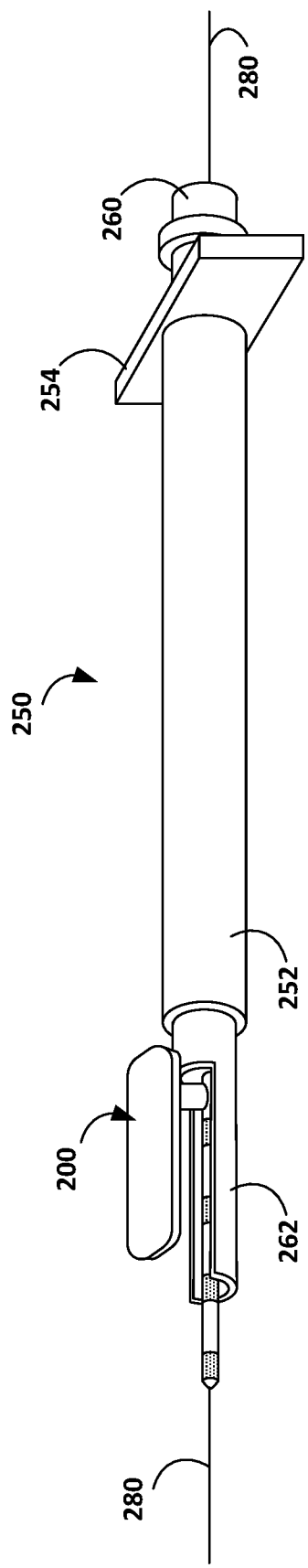
FIG. 6A is a perspective view of an implantable medical device loaded on an implant tool, according to an embodiment of the disclosure.
Figure 6B:
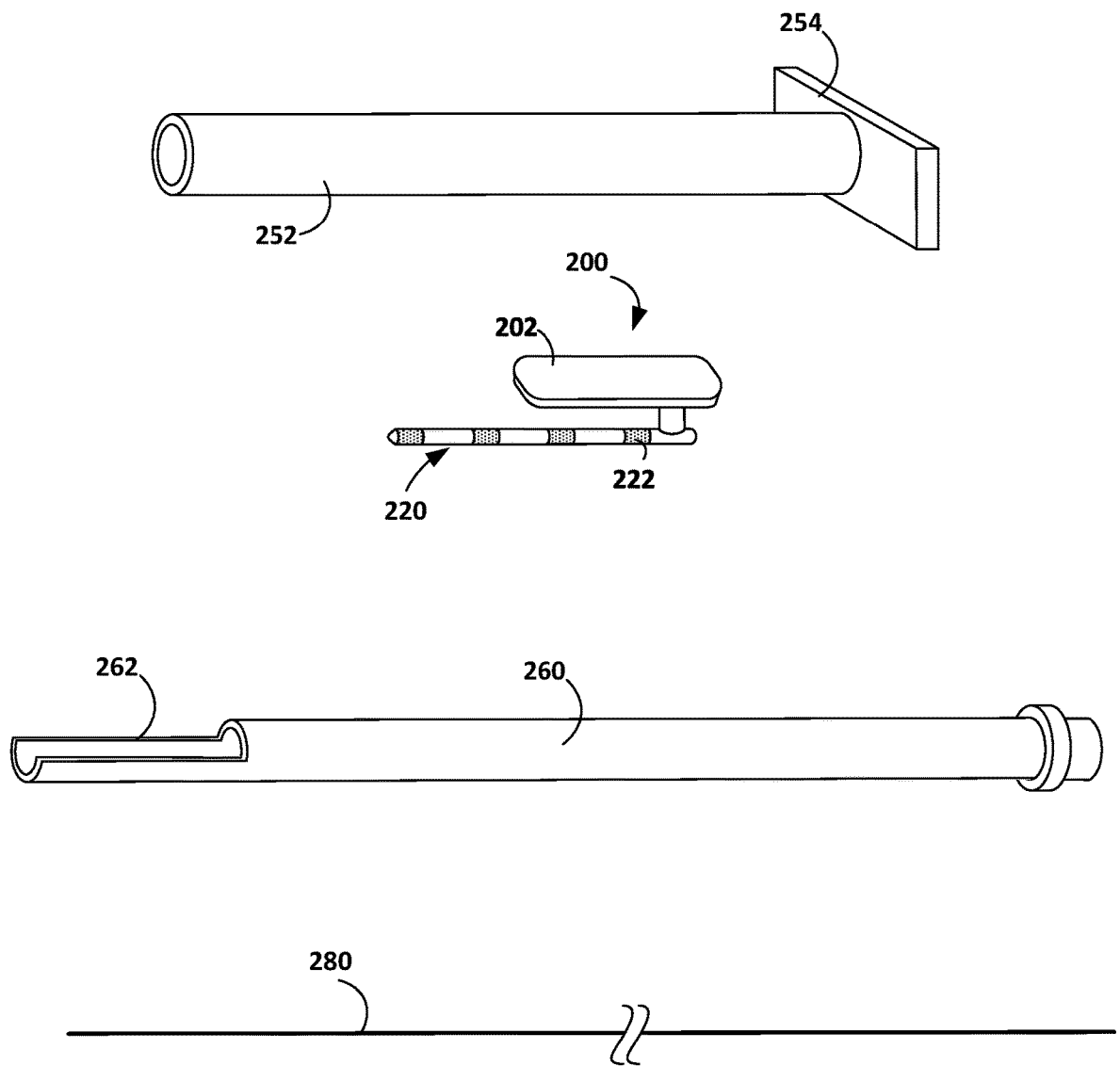
FIG. 6B is an exploded view of the components of FIG. 6A.

In an example, a tool 250 as depicted in FIGS. 6A-6B can be utilized to implant IMD 200 within a patient. Tool 250 includes an outer elongated sheath 252 having a handle 254, and an inner sheath 260 releasably and slidingly engageable with outer sheath 252. Inner sheath 260 includes a cradle 262 configured to selectively carry IMD 200 or a portion thereof.

Figure 7C:
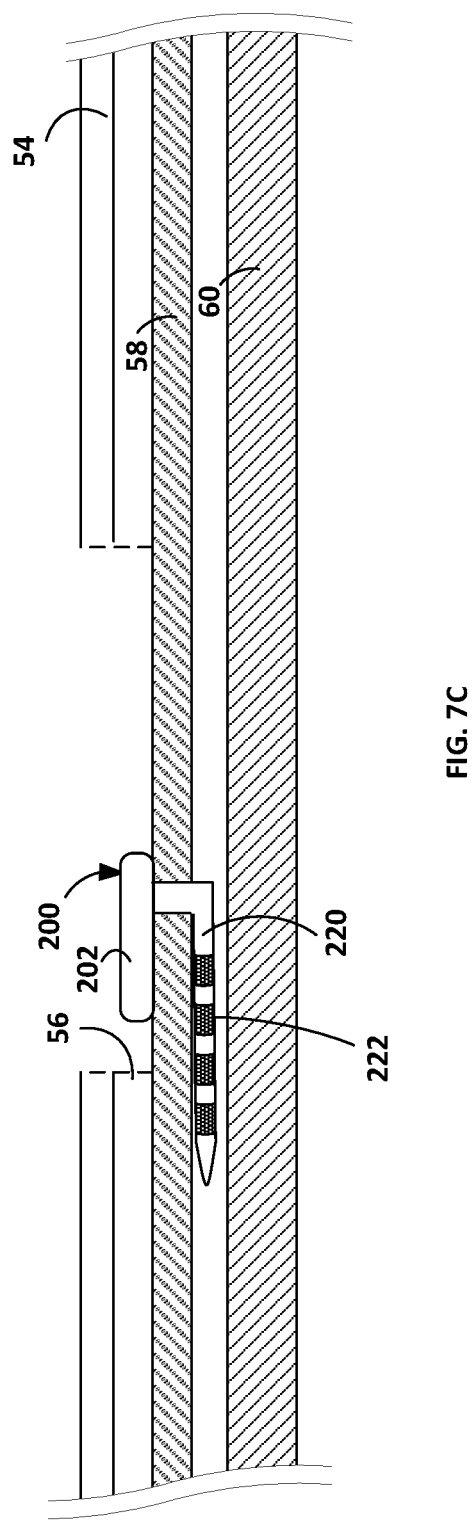

Referring now to FIGS. 7A-7C, a method of implanting IMD 200 proximate a tibial nerve will be described. On an ankle 50 of a patient, a first incision 52 in skin 54 is made. First incision 52 can be a one to three cm vertical incision superior and posterior to a medial malleolus and above a tibial nerve 60 on a medial aspect of ankle 50. With first incision 52 made, a medical practitioner can dissect down through fat layers 56 to fascia 58 as needed.

In an example, with fascia 58 exposed, a small second incision or nick 70 is made in fascia 58 at an inferior end (toward a heel of the patient) of the dissected area using a scalpel or similar device. In another example, a guidewire 280 can be inserted directly through fascia 58, and advanced downward (towards the heel) and inward on a path that is parallel to a tibia and tibial nerve 60. In an example, guidewire 280 is inserted at a point towards a superior end (closest to the knee) of first incision 52. Proper insertion depth and trajectory of guidewire 280 may be determined in a number of ways, including referencing anatomical landmarks such as the tibia or Achilles tendon, or utilizing ultrasound imaging, or by connecting guidewire 280 to an external pulse generator and observing sensory or motor responses of the patient to test stimulation.

With guidewire 280 appropriately positioned, IMD 200 can be loaded in cradle 262 of tool 250, as depicted in FIG. 6A. In an example, IMD 200 may be provided loaded in cradle 262, such as part of a kit. Tool 250 and IMD 200 are then advanced onto guidewire 280 such that guidewire 280 is disposed within guidewire passageway 240 of IMD 200. Tool 250 and IMD 200 are further advanced along guidewire 280 to the implant site until lead 220 is proximate fascia 58. A practitioner can then grasp inner sheath 260 of tool 250 and advance outer sheath 252 towards fascia 58, thereby inserting lead 220 through fascia 58 along guidewire 280 such that lead 220 is below fascia 58 while housing 202 remains outside of fascia 58, such as depicted in FIGS. 7B and 7C.

Optional testing of IMD 200 may be performed to determine if lead 220 has been properly positioned close to tibial nerve 60 to elicit a desired response from an applied electrical stimulation. In an example, IMD 200 is controlled by an external programmer to deliver test stimulation, and one or more indicative responses are monitored, such as toe flexion from simulation of the tibial motor neurons controlling the flexor hallucis brevis or flexor digitorum brevis, or a tingling sensation in the heel or sole of the foot excluding the medial arch. If such testing does not elicit appropriate motor or sensory responses, the practitioner should withdraw and reposition lead 220 and retest.

Once a practitioner has determined lead 220 is properly positioned to provide an appropriate patient response to delivered stimulation therapy, housing 202 can be secured in place. In an example, a suture or similar surgical fastening means can be attached between an anchor feature of housing 202 and surrounding tissue of the patient. Thus IMD 200 is therefore fixed in position at two points, with housing 202 secured by way of an anchor feature and lead 220 secured by an interference fit through fascia 58. First incision 52 can then be closed by appropriate means.

An advantage of the devices and methods described herein can be improved patient safety and satisfaction after implant. By making first incision 52 superior to medial malleolus and directing the lead down toward the heel instead of up toward the knee allows for faster and safer tissue healing. Body tissues higher up on the ankle are thicker and heal faster than tissues lower down, and the wearing of shoes by the patient will be less likely to interfere with a wound site superior to the medial malleolus than lower down at the level of the medial malleolus.

Figure 8:
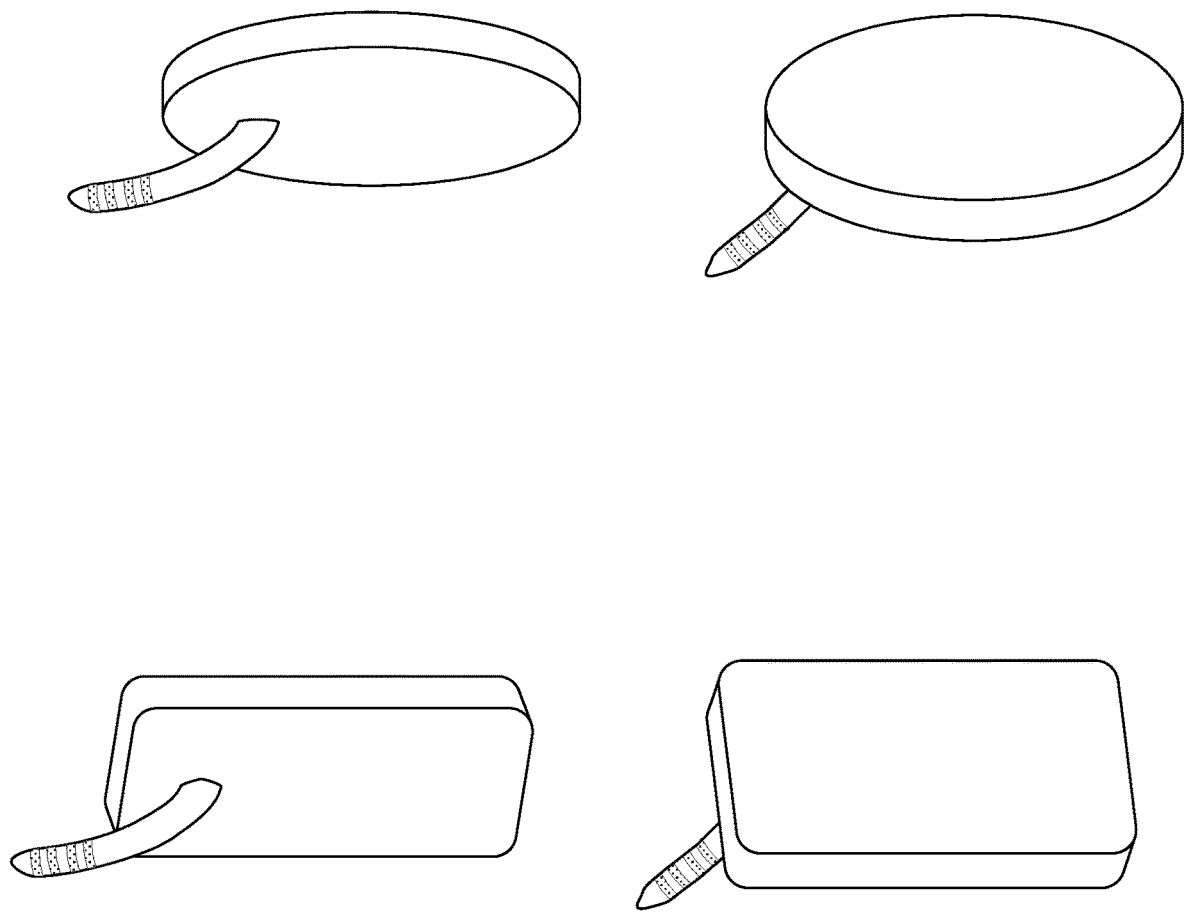
FIG. 8 depicts additional form factors for implantable medical devices according to other embodiments of the disclosure.

Referring now to FIG. 8, depicted are alternate form factors for an IMD as described and disclosed herein.

In one example, an IMD and implant tool are provided together as part of a kit. In another example, a kit may include instructions for implanting, programming or operating the system, the instructions being recorded on a tangible medium or including indications linking a user to electronically accessible instructions.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A method of implanting a tibial nerve stimulation device in an ankle region of a patient, the tibial nerve stimulation device including a housing and an electrical lead coupled to the housing, the electrical lead offset from the housing and including at least one electrode, a longitudinal axis of the housing generally oriented in the same direction as a longitudinal axis of the electrical lead, the method comprising:
  creating a first incision, in a skin of a patient superior and posterior to a medial malleolus on an ankle of the patient;
  creating a second incision, in a fascia layer in the ankle of the patient, the second incision being smaller than the first incision and the second incision sized to allow passage of the electrical lead therethrough; and
  advancing the implantable tibial nerve stimulation device through the first incision downward towards a heel of the patient and inward such that the electrical lead passes through the second incision, such that the housing of the implantable tibial nerve stimulation device is positioned superficial to the fascia layer and such that the at least one electrode is positioned below the fascia.

2. The method of claim 1, further comprising advancing the implantable tibial nerve stimulation device through the first incision over a guidewire.

3. The method of claim 1, wherein the electrical lead of the tibial nerve stimulation device includes a guidewire passageway extending from a proximal end of the electrical lead to a distal end of the electrical lead and being open on both ends such that a guidewire can extend outward from each end with the lead coupled to the housing, the method further comprising:

advancing the implantable tibial nerve stimulation device through the first incision over a guidewire via the guidewire passageway in the electrical lead.

4. The method of claim 1, further comprising implanting the implantable tibial nerve stimulation device such that the electrical lead longitudinal axis is generally oriented in the same direction as the housing longitudinal axis when implanted.

5. The method of claim 1, wherein advancing the implantable tibial nerve stimulation device is performed using an implant tool including an outer sheath and an inner sheath, the inner sheath including a cradle portion configured to selectively carry the implantable tibial nerve stimulation device, the method further comprising:

advancing the outer sheath of the implant tool toward a target implant location with respect to the inner sheath so as to deliver the implantable tibial nerve stimulation device to the target implant location.

6. The method of claim 1, further comprising:

performing testing of the implantable tibial nerve stimulation device, the testing including delivering a test stimulation and measuring an indicative patient response to the test stimulation.

\* \* \* \* \*